United States Patent [19]

Luminari

[11] Patent Number: 4,984,172
[45] Date of Patent: Jan. 8, 1991

[54] SYSTEM FOR DETECTING AND CORRECTING DEFECTS IN ARTICLES BEING PROCESSED, IN PARTICULAR WOOD PANELS WITH SPLITS, KNOT-HOLES, ETC.

[75] Inventor: Massimo Luminari, Lesmo, Italy

[73] Assignee: Lorenzo Cremona, Milano, Italy

[21] Appl. No.: 526,695

[22] Filed: May 21, 1990

Related U.S. Application Data

[63] Continuation of Ser. No. 407,682, Sep. 14, 1989, abandoned, which is a continuation of Ser. No. 199,352, May 26, 1988, abandoned, which is a continuation-in-part of Ser. No. 19,610, Feb. 27, 1987, abandoned.

[30] Foreign Application Priority Data

Mar. 21, 1986 [IT] Italy .............................. 19823 A/86

[51] Int. Cl.⁵ .............................................. G06F 15/20
[52] U.S. Cl. ..................................... 364/478; 144/332; 144/356; 250/563; 364/507
[58] Field of Search ............... 364/468, 469, 478, 507, 364/474.09; 144/332, 356, 357; 358/101, 106, 107, 903; 250/571, 572, 568, 548, 562, 552, 563; 356/429–431

[56] References Cited

U.S. PATENT DOCUMENTS

| Re. 26,653 | 8/1969 | Skoog | 144/332 |
|---|---|---|---|
| 3,547,170 | 12/1970 | Maxey et al. | 144/332 |
| 3,976,384 | 8/1976 | Matthews et al. | 250/563 X |
| 4,149,089 | 4/1979 | Idelsohn et al. | 144/356 X |
| 4,188,544 | 2/1980 | Chasson | 144/357 X |
| 4,424,530 | 1/1984 | Taylor | 364/572 X |
| 4,498,778 | 2/1985 | White | 364/571 X |
| 4,614,555 | 9/1986 | Smith et al. | 144/332 X |

Primary Examiner—Joseph Ruggiero
Attorney, Agent, or Firm—Finnegan, Henderson, Farabow, Garrett & Dunner

[57] ABSTRACT

Apparatus for detecting and correcting defects in plywood panels carried on a conveyor including a defect detection and measuring device for scanning the surface of the panels to detect and measure the defects; a plurality of correcting units downstream of the device for correcting the defects, and control devices for receiving data from the detection and measuring device and controlling operation of the correcting units to remove and patch the defects, wherein the detection and measuring means projects a light beam transversely onto the surface of the panels and the reflected beam is resolved into a series of points, the position of each of which is measured with respect to the X, Y and Z axes to determine the size of the defect and the ratio of the light intensity of each point with the mean of the light intensity of all points of the reflected beam is measured to determine the type of defect.

3 Claims, 5 Drawing Sheets

SYSTEM FOR DETECTING AND CORRECTING DEFECTS IN ARTICLES BEING PROCESSED, IN PARTICULAR WOOD PANELS WITH SPLITS, KNOT-HOLES, ETC.

This application is a continuation of application Ser. No. 07/407,682 filed Sept. 14, 1989, abandoned, which is a continuation of Ser. No. 07/199,352 filed May 26, 1988 (now abandoned), which is a C-I-P of Ser. No. 07/019,610, filed Feb. 27, 1987 (now abandoned).

The present invention relates to a system for automatically detecting and correcting defects in articles being processed, in particular plywood panels with splits, knot-holes, etc. requiring to be satisfactorily plugged.

As is well-known to persons skilled in the art, a plywood panel production line includes a defect detection and plugging station, the defects in question being splits, knot-holes and the like, which can always occur in this type of article.

The operations of detection and plugging have to date been carried out by production line operators using entirely manual methods. In such cases, assessment of the defects by the operator is subjective; and when the assessment has been made the operator himself plugs the defects manually, using suitable equipment.

This mode of operating means that, if it is wished to keep output at acceptable levels, a large workforce must be employed and this in turns means that the plugging operation has a very high incidence on the final cost of each panel. Additionally, the operator's assessment and plugging of the defect are not always optimal.

The general object of the present invention is to obviate the aforementioned drawbacks by embodying a system that will fully automate the operations in question, minimizing the workforce required.

To attain this object, the invention according to the present application embodies a system for detecting and correcting defects in articles being processed, in particular wood panels carried by a conveyor, wherein there are used in combination: one or more defect detection and identification devices, described in greater detail hereinafter, one or more defect correction devices, also described in more detail hereinafter, and appropriate means for data processing and for generating automated controls interposed between the said defect detection devices and the said defect correction devices.

The structural and functional characteristics of the invention, and its advantages over the known art, will become more apparent from an examination of the following illustrative and not limiting description, referred to the appended diagrammatic drawings, in which.

Figure 1:
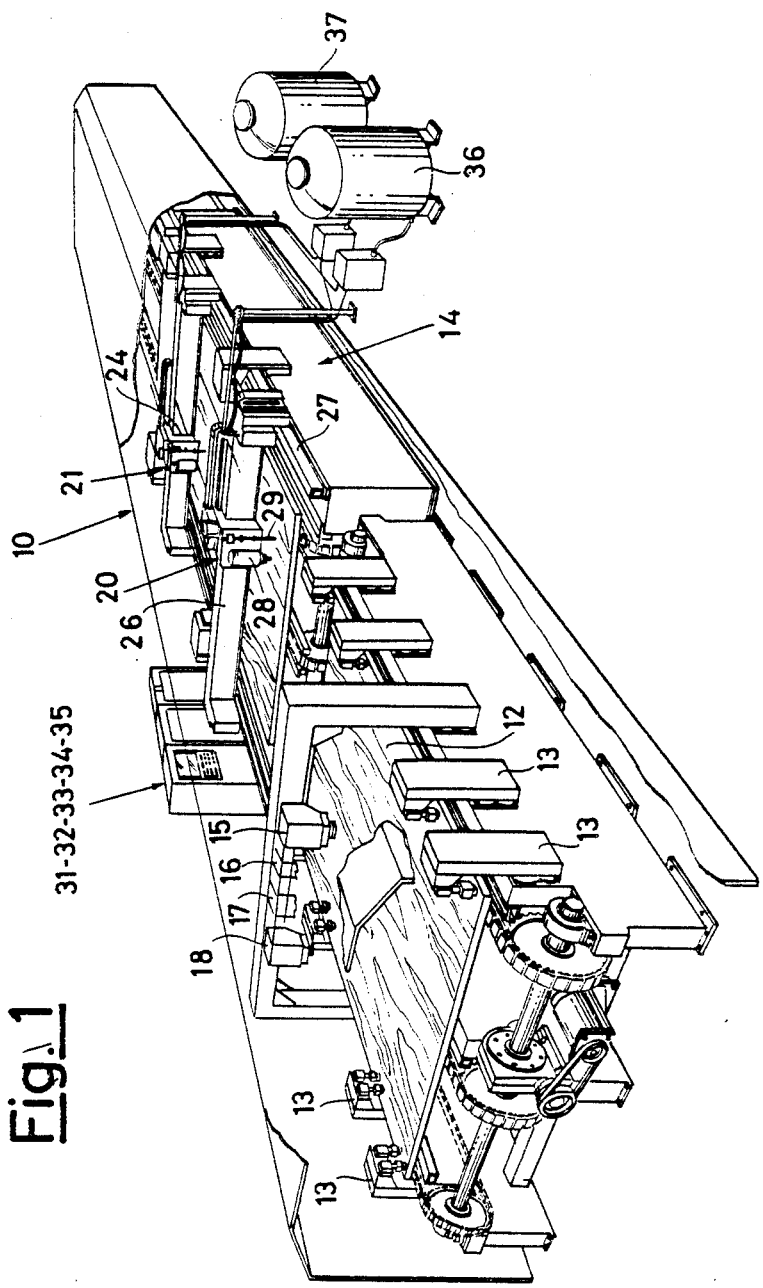
FIG. 1 is a perspective view of an apparatus for the embodiment of the system according to the invention for the detection and correction of defects present in the plywood panel.
Figure 2:
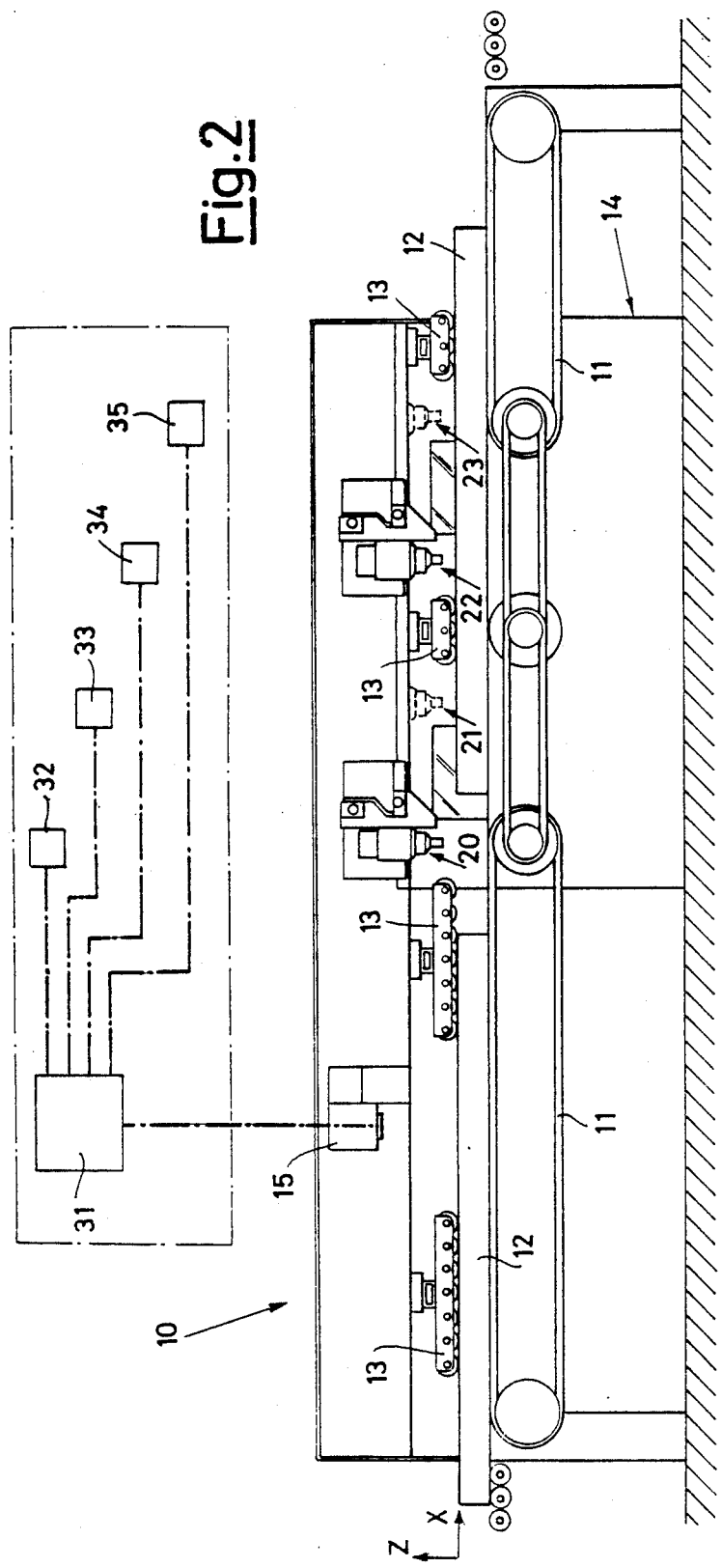
FIG. 2 is a longitudinal elevational view.
Figure 3:
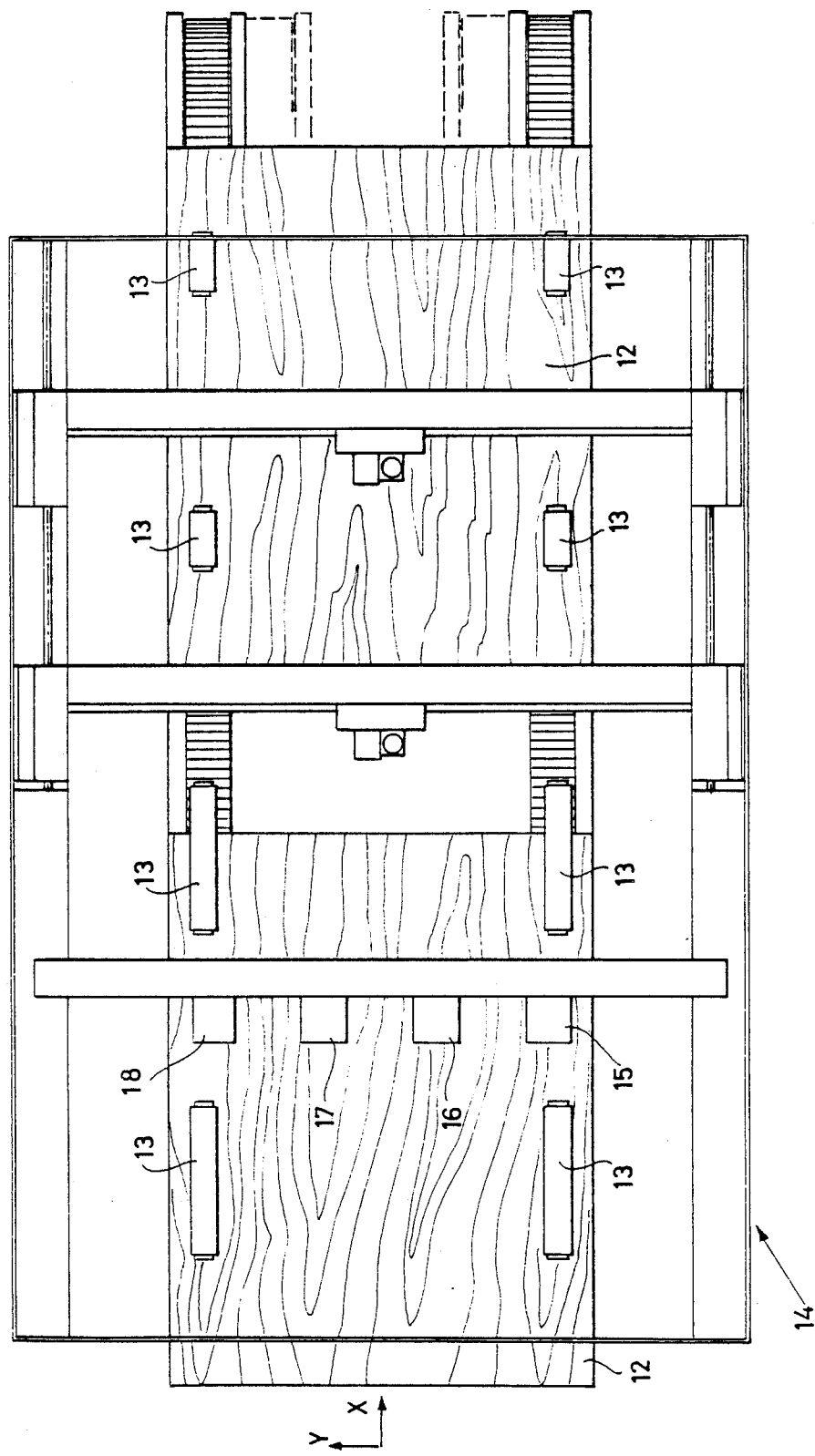
FIG. 3 is a plan view.
Figure 4:
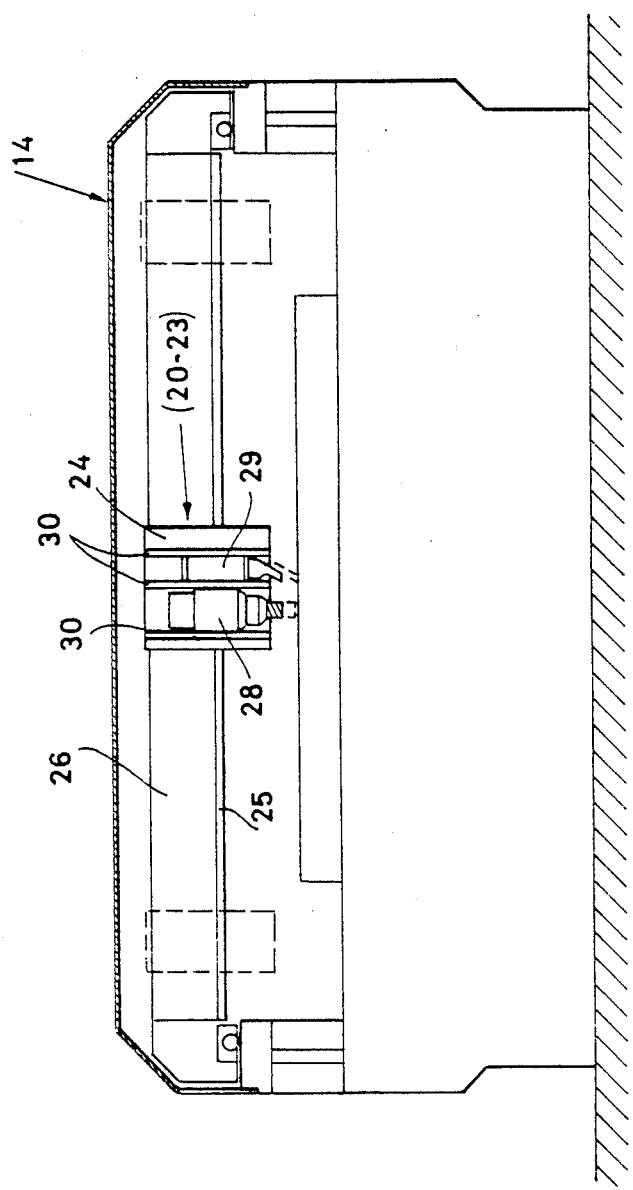
FIG. 4 is a cross section of the apparatus.

With reference to the drawings, the said apparatus is indicated overall by 10 and structurally consists of a powered belt conveyor 11 on which wood panels 12 for processing are positioned and pressed by pressors 13 and fed step-wise by pre-established distances. Conveyors of this type are well-known and are therefore not herein described in detail.

The conveyor 11 is supported by a frame 14 on which there is mounted one or more defect detection devices 15, 16, 17, 18 which can scan the surface of the underlying panel 12.

Downstream of the detection devices 15–18 there are provided respective operating complexes 20, 21, 22 and 23, each supported by a slide 24 which moves transversally on guides 25 of a crossmember 26 which can in turn move longitudinally on guides 27 of the frame 14.

Each operating complex 20–23 comprises a powered tool 28 and a plugging device 29, each movable vertically on guides 30. The tools 28 and devices 29 can thus move longitudinally, transversally and vertically with respect to the underlying panels 12, i.e. along the three Cartesian coordinates X, Y and Z.

The defect detection devices 15–18 are operatively connected to a respective operating complex 20–23 through the intermediary of a processor 31 the outputs of which transmit to a plurality of numerical control units 32, 33, 34 and 35, which control the said complexes.

The processor 31 and the numerical control 32–35 are electronic devices of known type and known characteristics and are widely used in many sectors of the art, and for this reason are not here further described.

The numeral 36 and 37 indicate two reservoirs containing compounds suitable for forming the plugging material which is fed to the plugging devices 29.

The mode of operation of the system described above is briefly as follows. Motion is imparted to the belt conveyors 11 for example by a permanent-magnet motor (panel translation axis). An encoder connected to the motor establishes the longitudinal position of the panel. The distance between the lateral supports can be varied and adjusted in relation to the width of the workpiece.

The stepwise feed of the panel is for example programmed for maximum steps of 600 mm, and during this stage the panel is scanned by devices 15–18 which effect real time identification of defects and send the corresponding data to the processor unit 31.

The data detected by detection devices are processed by the processing unit 31 which transmits signals to the numerical control units 32–35, which then control the respective operating complexes 20–23.

As mentioned, each operating complex can be embodied with two heads for, respectively, milling, sanding and plugging with stoppers or resins any holes present from the outset and/or caused subsequently by processing tools, thus correcting the defects detected by the previous scanning operation.

The heads move along the axes X, Y, Z, controlled by permanent-magnet motors, ballscrews and on slide guides.

At maximum operating capacity, a plurality of simultaneously operating heads are employed.

Preferably, provision is also made for a high-efficiency exhaust system, with tool shrouding, for the removal of chips, dust, etc. occuring during processing.

The number of operating modules of which the system is composed is determined by the output required and the number of defects on the surfaces of the panels.

During defect correction operations, the panels are held firm on a support surface.

Figure 5:
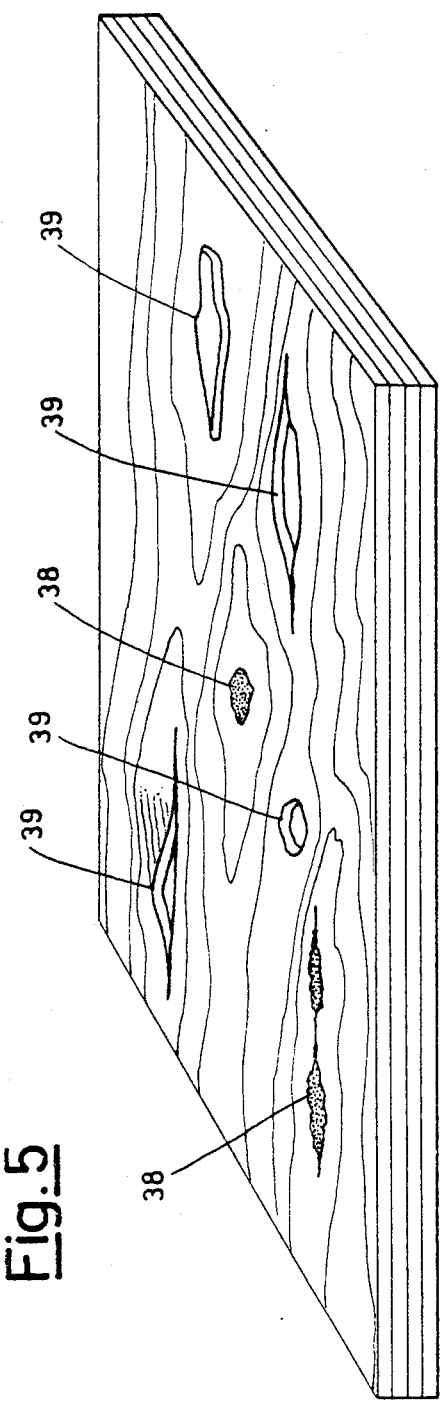
FIG. 5 is a diagrammatic illustration of the principal defects typically found on the surface of a playwood panel.
Figure 6:
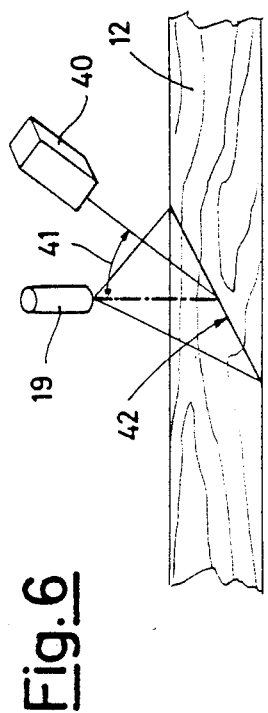
FIG. 6 is a detail of each of the devices 15–18.

The essential part of the present invention is the defect detection and identification system. As illustrated diagrammatically in FIG. 5 of the drawings, the said defects typically fall into two categories:

(a) defects consisting of over-accentuated chromatic discontinuities on the surface of the panel, such as dark knots, glue or paint stains or spots or stains or spots of other substances with which the panel has accidentally been in contact, and so on. This category of defects is collectively indicated by the numeral 38.

(b) defects consisting of over-accentuated geometrical discontinuities on the surface of the panel, such as long splits, round holes, normally knot-holes caused by the coming away of knots on the surface layer of the panel, protruberance more or less irregular in shape due for example to imperfect joining of the veneers making up the surface layer of the panel or due to splinters of wood left glued to the surface of the panel, and so on. This category of defects is collectively indicated by the numeral 39. The detection system in question must be able to distinguish the type 38 defects from the type 39 defects, and must measure the extension of each along the three controlled axes X, Y, Z so as to send to the processor 31 the information required to appropriately operate the control-units 32–35 and thus to actuate the devices 28 and 29 to obtain the effect strictly necessary for correcting the defect without waste of wood or plugging material.

To such end, provision is made in each of the devices 15–18 for an element 19 (for example a LASER projector) which projects transversally on the surface of the panel 12 a light beam 42 which is read at a given angle 41 to the axis of projection by an element 40 (for example a CCD chamber or the like) capable of resolving the said beam into a series of points, the position of each of which is determined with respect to the system of coordinates X, Y, Z and measurement is made of the ratio between the light-intensity of each point and the mean of the light-intensity of all the points of the beam. Two cases can thus occur:

(a) the positions of all the points are aligned along a straight line (i.e. they all have the same coordinate $Z=0$ for each position of the panel defined by the coordinate X), but some of the points have a light-intensity very different from the mean: what is here involved therefore is one or more type 38 defects, and their extension along the aforesaid straight line is measured by the coordinates Y of the aforesaid points.

(b) all the points of the beam 42 have the same light-intensity but some of them have the coordinate Z different from zero: what is in this case involved, therefore, is one or more type 39 defects, the extension of which along the line of projection is measured by the coordinates Y of the aforesaid points, and the depth (or protruberance) of which is measured by the coordinates Z of the same points.

The identification of the defects as such is determined by the exceeding of given thresholds in the deviations between the light-intensity values and between the values of the coordinates Z relative to the single points, and such thresholds are pre-set and memorized in the processor 31.

I claim:

1. In an apparatus for detecting and correcting defects in plywood panels including conveyor means for translating the panels along a path in the X direction, defect detection means for scanning the surface of the panels to locate defects therein, correcting means downstream of the detection means for removing portions of said panel corresponding to the detected defects and for patching the removed portions with a flowable plugging material as the panel moves along said path and control means operatively connected between the detection means and the correcting means for operating the correcting means to correct the defects, wherein the improvement comprises at least one defect detection and measuring device for measuring the length, width and depth of the defects in the panels in the X, Y and Z axes respectively, said detection and measuring device comprising means for projecting a light beam transversely onto the surface of the panels and means for receiving the reflected beam at a given angle with respect to the axis of projection and for resolving the said reflected beam into a series of points, said receiving means measuring the position of each point with respect to the X, Y and Z axes and the ratio between its light intensity and the mean of the light intensity of all points of the reflected beam to thereby determine the length, width and depth of each defect.

2. The apparatus of claim 1, comprising a plurality of pairs of detection and measuring devices and corresponding correcting means and a separate control means for each said pair.

3. A defect detection and measuring device for use in an apparatus for detecting and correcting defects in plywood panels that measures the length, width and depth of the defects in the panels in the X, Y and Z axes respectively, said device comprising means for projecting a light beam transversely onto the surface of the panels and means for receiving the reflected beam at a given angle with respect to the axis of projection and for resolving the said reflected beam into a series of points said receiving means measuring the position of each point with respect to the X, Y and Z axes and the ratio between its light intensity and the mean of the light intensity of all points of the reflected beam to thereby determine the length, width and depth of each defect.

* * * * *